United States Patent
Swaelens et al.

(10) Patent No.: US 8,038,440 B2
(45) Date of Patent: Oct. 18, 2011

(54) METHOD FOR PLACING AND MANUFACTURING A DENTAL SUPERSTRUCTURE, METHOD FOR PLACING IMPLANTS AND ACCESSORIES USED THEREBY

(75) Inventors: Bart Filip Jos Swaelens, Putte (BE); Luc Vrielinck, Genk (BE); Carl Van Lierde, Leuven (BE)

(73) Assignee: Materialise Dental N.V., Leuven (BE)

( * ) Notice: Subject to any disclaimer, the term of this patent is extended or adjusted under 35 U.S.C. 154(b) by 648 days.

(21) Appl. No.: 10/546,702

(22) PCT Filed: Feb. 23, 2004

(86) PCT No.: PCT/BE2004/000024
§ 371 (c)(1),
(2), (4) Date: Aug. 24, 2005

(87) PCT Pub. No.: WO2004/075771
PCT Pub. Date: Sep. 10, 2004

(65) Prior Publication Data
US 2006/0093988 A1    May 4, 2006

Related U.S. Application Data

(60) Provisional application No. 60/450,672, filed on Mar. 3, 2003, provisional application No. 60/495,731, filed on Aug. 18, 2003.

(30) Foreign Application Priority Data

Feb. 28, 2003  (BE) .................................. 2003/0132

(51) Int. Cl.
*A61C 3/02*  (2006.01)

(52) U.S. Cl. .......................................................... 433/76
(58) Field of Classification Search .................... 433/69, 433/76, 172, 173, 72, 75, 215, 225, 229, 433/201.1
See application file for complete search history.

(56) References Cited

U.S. PATENT DOCUMENTS

| | | | |
|---|---|---|---|
| 4,109,382 A | 8/1978 | Koch | |
| 4,872,840 A | 10/1989 | Bori | |
| 4,955,811 A | 9/1990 | Lazzara et al. | |
| 4,988,297 A | 1/1991 | Lazzara et al. | |
| 5,102,271 A | 4/1992 | Hemmings | |
| 5,133,660 A * | 7/1992 | Fenick | 433/76 |
| 5,184,926 A | 2/1993 | Hemmings | |
| 5,213,502 A | 5/1993 | Daftary | |
| 5,215,460 A * | 6/1993 | Perry | 433/75 |
| 5,259,759 A | 11/1993 | Jörnéus et al. | |

(Continued)

FOREIGN PATENT DOCUMENTS

BE              09400399              4/1994

(Continued)

OTHER PUBLICATIONS

International Search Report, PCT/BE2004/000024 (mailed Jul. 23, 2004).

(Continued)

*Primary Examiner* — Cris L Rodriguez
*Assistant Examiner* — Heidi M Eide
(74) *Attorney, Agent, or Firm* — Clark & Elbing LLP

(57) ABSTRACT

Methods for placing and manufacturing a dental superstructure, and methods for placing implants and accessories used thereby.

13 Claims, 6 Drawing Sheets

U.S. PATENT DOCUMENTS

| | | | |
|---|---|---|---|
| 5,320,529 A * | 6/1994 | Pompa | 433/76 |
| 5,520,688 A | 5/1996 | Lin | |
| 5,554,027 A | 9/1996 | Brånemark | |
| 5,562,448 A | 10/1996 | Mushabac | |
| 5,564,925 A | 10/1996 | Shampanier et al. | |
| 5,584,694 A | 12/1996 | Forsmalm et al. | |
| 5,613,852 A | 3/1997 | Bavitz | |
| 5,662,473 A | 9/1997 | Rassoli et al. | |
| 5,674,071 A | 10/1997 | Beaty et al. | |
| 5,685,714 A | 11/1997 | Beaty et al. | |
| 5,725,376 A * | 3/1998 | Poirier | 433/75 |
| 5,733,122 A | 3/1998 | Gordon | |
| 5,769,636 A | 6/1998 | Di Sario | |
| 5,800,168 A * | 9/1998 | Cascione et al. | 433/75 |
| 5,813,858 A | 9/1998 | Singer | |
| 5,823,778 A * | 10/1998 | Schmitt et al. | 433/214 |
| 5,871,356 A | 2/1999 | Guedj | |
| 5,967,777 A * | 10/1999 | Klein et al. | 433/75 |
| 5,989,025 A | 11/1999 | Conley | |
| 5,989,258 A | 11/1999 | Hattori | |
| 6,062,856 A * | 5/2000 | Sussman | 433/76 |
| 6,319,000 B1 * | 11/2001 | Brånemark | 433/75 |
| 6,319,006 B1 | 11/2001 | Scherer et al. | |
| 6,361,537 B1 * | 3/2002 | Anderson | 606/86 B |
| 6,382,975 B1 | 5/2002 | Poirier | |
| 6,447,295 B1 | 9/2002 | Kumar et al. | |
| 6,514,258 B1 | 2/2003 | Brown et al. | |
| 6,692,254 B1 | 2/2004 | Kligerman et al. | |
| 6,814,575 B2 * | 11/2004 | Poirier | 433/75 |
| 2002/0102517 A1 * | 8/2002 | Poirier | 433/173 |
| 2002/0137003 A1 | 9/2002 | Knapp | |
| 2004/0146830 A1 | 7/2004 | Weinstein | |
| 2005/0106534 A1 | 5/2005 | Gahlert | |
| 2005/0170311 A1 | 8/2005 | Tardieu et al. | |
| 2006/0040233 A1 | 2/2006 | Weinstein et al. | |
| 2006/0093988 A1 | 5/2006 | Swaelens et al. | |
| 2006/0275736 A1 | 12/2006 | Wen et al. | |
| 2007/0160953 A1 | 7/2007 | Tardieu | |
| 2009/0187393 A1 | 7/2009 | Van Lierde et al. | |

FOREIGN PATENT DOCUMENTS

| | | |
|---|---|---|
| BE | 1 011 205 | 6/1999 |
| DE | 299 17 458 U1 | 1/2000 |
| DE | 100 36 027 A1 | 1/2002 |
| EP | 640 322 | 3/1995 |
| JP | 2000-512868 | 10/2000 |
| WO | WO 92/03984 | 3/1992 |
| WO | WO 97/10770 | 3/1997 |
| WO | WO 97/49351 | 12/1997 |
| WO | WO 99/26540 | 6/1999 |
| WO | WO 00/25695 | 5/2000 |
| WO | WO 03/071972 | 9/2003 |
| WO | WO 2004/064660 | 8/2004 |
| WO | WO 2004/065893 | 8/2004 |
| WO | WO 2004/075771 | 9/2004 |
| WO | WO 2005/053564 | 6/2005 |
| WO | WO 2006/115841 | 11/2006 |
| WO | WO 2007/134701 | 11/2007 |

OTHER PUBLICATIONS

Written Opinion of the International Searching Authority, PCT/BE2004/000024 (mailed Jul. 23, 2004).
International Preliminary Report on Patentability, PCT/BE2004/000024 (completed Sep. 19, 2005).
International Preliminary Report on Patentability for PCT/EP2004/013435, completed Mar. 16, 2006.
International Preliminary Report on Patentability for PCT/FR2003/000667, completed Oct. 17, 2003.
International Search Report for PCT/EP2004/013435, mailed Sep. 15, 2005.
International Search Report for PCT/FR2003/000667, mailed Jul. 28, 2003.
Klein et al., "Computer-Guided Surgery Utilizing a Computer-Milled Surgical Template," *Pract. Proced. Aesthet. Dent.* 13(2): 165-169 (2001).
Office Action for U.S. Appl. No. 10/505,846, mailed Mar. 21, 2008.
Office Action for U.S. Appl. No. 10/596,124, mailed Dec. 5, 2007.
Response to Written Opinion for PCT/EP2004/013435, filed Jul. 20, 2005.
Written Opinion of International Searching Authority for PCT/EP2004/013435, mailed Jul. 4, 2005.
Communication from European Patent Office regarding EP 04 713 496.0, dated Jan. 22, 2009.
International Preliminary Report on Patentability (PCT/EP2007/003810), completed Nov. 14, 2008.
International Search Report (PCT/EP2007/003810), mailed Oct. 9, 2007.
Office Action for U.S. Appl. No. 10/505,846, mailed Nov. 6, 2008.
Translation of International Preliminary Report on Patentability (PCT/FR2003/000667), completed Oct. 17, 2003.
Written Opinion of the International Searching Authority (PCT/EP2007/003810), mailed Oct. 9, 2007.
Office Action for U.S. Appl. No. 10/505,846, mailed Jun. 19, 2009.
Office Action for U.S. Appl. No. 10/596,124, mailed Dec. 18, 2008.
Office Action for U.S. Appl. No. 10/596,124, mailed Jun. 19, 2009.
Translation of Notice of Grounds of Rejection for Japanese Patent Application No. 501389/2006, drafted Feb. 19, 2009.
Office Action for Canadian Patent Application No. 2,477,107, dated Oct. 5, 2009.
Notice of Grounds of Rejection for Japanese Patent Application No. 2006-501389, dated Jan. 26, 2010.
English Translation of the Notice of Grounds of Rejection for Japanese Patent Application No. 2006-501389, dated Jan. 26, 2010.
Notice of Preliminary Rejection for Korean Patent Application No. 10-2004-7013405 issued by the KIPO, dated Oct. 28, 2009.
English Translation of the Notice of Preliminary Rejection for Korean Patent Application No. 10-2004-7013405 issued by the KIPO, dated Oct. 28, 2009.
Office Action for U.S. Appl. No. 10/505,846, mailed May 4, 2010.
Advisory Action for U.S. Appl. No. 10/505,846 dated Sep. 17, 2010.
Office Action for U.S. Appl. No. 12/421,919, mailed Aug. 18, 2010.
Office Action U.S. Appl. No. 12/421,919 mailed Apr. 29, 2011.
Office Action for Canadian Patent Application No. 2,477,107 dated Dec. 15, 2010.

* cited by examiner

METHOD FOR PLACING AND MANUFACTURING A DENTAL SUPERSTRUCTURE, METHOD FOR PLACING IMPLANTS AND ACCESSORIES USED THEREBY

CROSS REFERENCE TO RELATED APPLICATIONS

This application is the U.S. National Stage of International Application No. PCT/BE2004/000024, filed Feb. 23, 2004, which, in turn, claims the benefit of Belgian patent application 2003/0132, U.S. provisional patent application No. 60/450,672, and U.S. provisional patent application No. 60/495,731 filed Feb. 28, 2003, Mar. 3, 2003, and Aug. 18, 2003, respectively.

The present invention concerns a method for placing and manufacturing a dental superstructure. This is a structure which is fitted on implants, fixed in the bone of a patient, upon which artificial teeth have been or are provided.

It is known that when a number of teeth have to be built on more than one dental implant, a metal frame can be used to this end which fits on the implants, upon which the teeth can then be modeled in order to form the superstructure.

According to a conventional method for placing such a superstructure, implants are provided in the jaw, after which they are left to grow in for three to six months. After this osseo-integration, a mold or cast is taken of these implants or top pieces, called abutments, that have been fitted upon the latter. With this mold, the dental laboratory will then manufacture the superstructure with the accompanying teeth.

According to a known technique, use can hereby be made of an overdenture, whereby a metal structure is fit on the implants and the prosthesis is snapped in on this structure in order to form the final superstructure.

Use can also be made of a fixed superstructure with a metal frame, for example gold or cobalt chromium, which roughly already has the shape of the teeth, and upon which porcelain teeth are made.

Traditionally, the implants are left to grow in for three to six months, after which the gums are opened again and the superstructure, made on the basis of molds of the positioned implants, are fixed on the implants.

Recently, however, there is a tendency to refrain from letting the implants grow in for three to six months, and to immediately put a load on them, what is called 'immediate loading'.

The superstructure is hereby made, according to the methods known until now, by means of (i) a test arrangement in an articulator, which is used to determine the positions of the teeth and (ii) a mold of the implants in the mouth of the patient on the other hand.

This mold has to be made with great precision and the three-dimensional positions of the implants must be reproduced very precisely in the superstructure, since the different implants or the abutments provided upon them have to correspond exactly to the different points of contact in the superstructure.

Thus, the dental laboratory can only start manufacturing the superstructure after the mold has been taken. This implies that, with the present methods, it is not possible to fix the superstructure immediately after the implants have been placed, since the laboratory requires a number of days or weeks to manufacture it.

In order to solve this problem, a known technique is to use prefabricated standard superstructures in the shape of a horseshoe. According to this method, the normal operational flow is flipped upside down. Instead of adjusting the superstructure to the positioning of the implants, the implants are positioned in function of the superstructure. To this end, a drill jig is supplied with the superstructure. Both have a shape similar to that of a horseshoe. The bone is milled off thus providing a flat surface on which the drill jig is positioned. Next implant cavities are drilled on the places indicated by the jig.

Such a method, however, has a number of major disadvantages. The bone has to be milled off in order to allow positioning of the jig on the bone. This way of working is drastic and implies loss of bone, while in many cases the patients already lack bone.

Moreover, the shape of the jaw has to correspond to the shape of a horseshoe. Even if a number of models are made in the shape of a horseshoe, there will always be patients whose jaws do not have a shape corresponding with any of the predefined standards.

Further, the position of the implant is determined by the fitting jig. Consequently, the implant cavities will not always be drilled in the best place and more often than not end up in suboptimal places, for example where the bone is not very strong. Moreover, it is only possible to place the implants in a parallel way, which is not always the best position.

The present invention features a method for placing and manufacturing a dental superstructure. This method does not have the above-mentioned disadvantages and is simple and fast.

Therefore, the invention concerns a method for placing and manufacturing a dental superstructure, whereby (i) a computer planning is made of the position of the implants, (ii) one or several accessories are made on the basis of the computer planning by means of which the implants can be placed, and whereby (iii) on these implants, after they have been placed, the superstructure is fitted, characterized in that the superstructure is made, either directly or indirectly, on the basis of computer planning, which normally will be the same computer planning as described above.

By also realizing the superstructure on the basis of the computer planning, several advantages and new possibilities are created. Thus, for example, the superstructure can always be perfectly adjusted to the position of the implants. Moreover, it is no longer necessary to make direct molds from the patient after the implants have been placed. Further, it is also possible to realize the superstructure beforehand so, if required, it can be fitted on the implants immediately after they have been placed.

Manufacturing the superstructure directly or indirectly on the basis of a computer planning means that said computer planning is used to either form molding pieces for manufacturing the superstructure, to form the superstructure itself, or to form parts of such molding pieces or of such a superstructure.

It should be noted that the present invention also features a number of new techniques for placing one or more implants, irrespective of whether or not these techniques are used in combination with the production of a superstructure on the basis of a computer planning. Thus, for example, the invention also features a method for placing one or several implants, whereby a computer planning is made with reference to the position of the implants concerned, characterized in that, on the basis of this computer planning, one or several accessories are made by means of which the implants can be placed (i.e., drilling of the implant cavities and implant guidance). The method is hereby further characterized in that, for the aforesaid accessories, one or several accessories are made and/or used, selected from the following list:

an accessory in the shape of a drill jig in which one or several ducts are formed for drills, which are provided in the drill jig in function of the computer planning;

an accessory in the shape of a drill jig in which one or several ducts are formed for drills, which are provided in the drill jig in function of with respect to the computer planning, whereby means are also used in combination with at least one of these ducts, which make it possible to successively work with different drill diameters in one and the same duct;

an accessory as in the preceding paragraph, whereby the ducts have openings in which above-mentioned means can be placed, which make it possible to successively work with different drill diameters and whereby these means consist of interchangeable bushes with openings or passages of different diameters;

an accessory as in the preceding paragraph, whereby the ducts are laterally open to allow lateral insertion of a drill and whereby the interchangeable bushes preferably are placed over the drill prior to insertion and placed in the duct while drilling to provide guidance an accessory in the shape of a drill jig which is configured such that it also serves as a fitting jig;

an accessory in the shape of a drill jig which is configured such that it also serves as a positioning jig, and in particular can be used to force the implants into the required position after they have been placed;

an accessory which is made as a positioning jig which allows to force the forcing of the implants into the required position after they have been placed;

an accessory according to any of the two preceding paragraphs, whereby said the accessory is provided with passages for screws that can be screwed into the implants, whereby these passages and the accompanying screws have such a shape that, when the screws are tightened, they can be forced into a specific position;

an accessory which is made as an intermediate positioning jig which has at least features which allow for a connection with at least one implant that has already been placed, and which also has features forming a duct for a drill and/or an implant or features forming an implant placed on an implant holder.

Other details and advantages of the invention will emerge from the description that follows, as well as from the attached claims.

Naturally, the invention also concerns all of the parts described hereafter, used for realizing the method, such as accessories (for example, jigs, molding pieces, etc.).

Naturally, the invention also features a method for manufacturing such accessories, characterized in that the above-mentioned accessories are built by means of a computer planning.

With the intention of better showing the characteristics of the invention, hereafter as example without any limiting character, some preferred embodiments of a method for placing and manufacturing a dental superstructure according to the invention are described, with reference to the accompanying drawings, in which.

Figure 9:
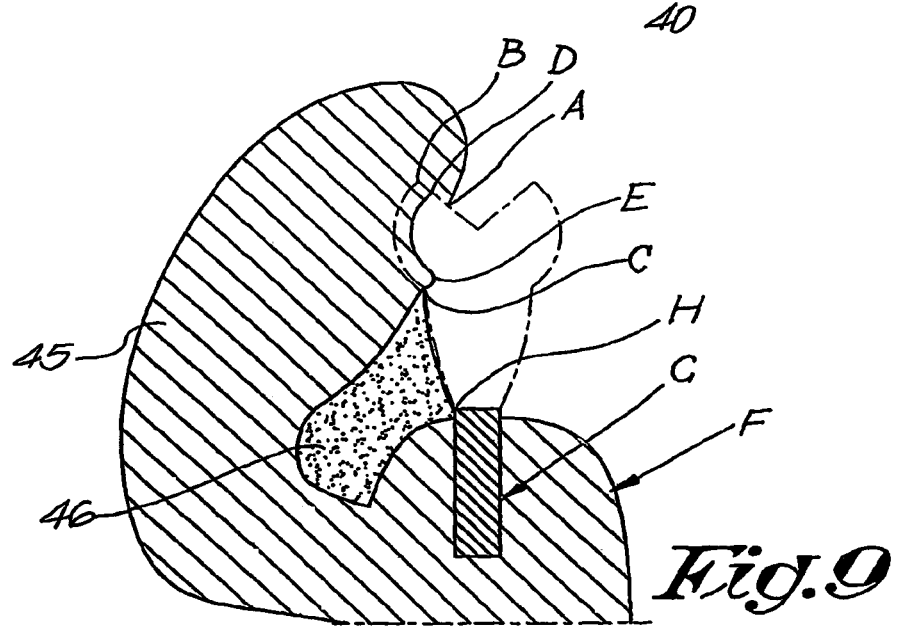
Figures 10, 11:
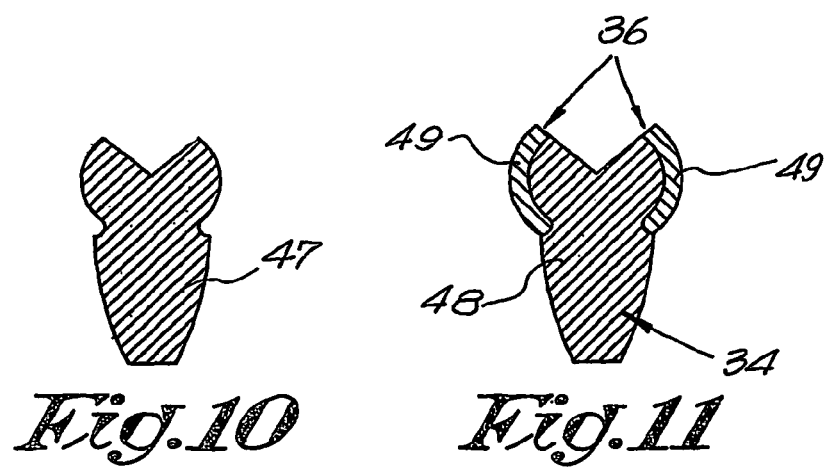
Figure 12:
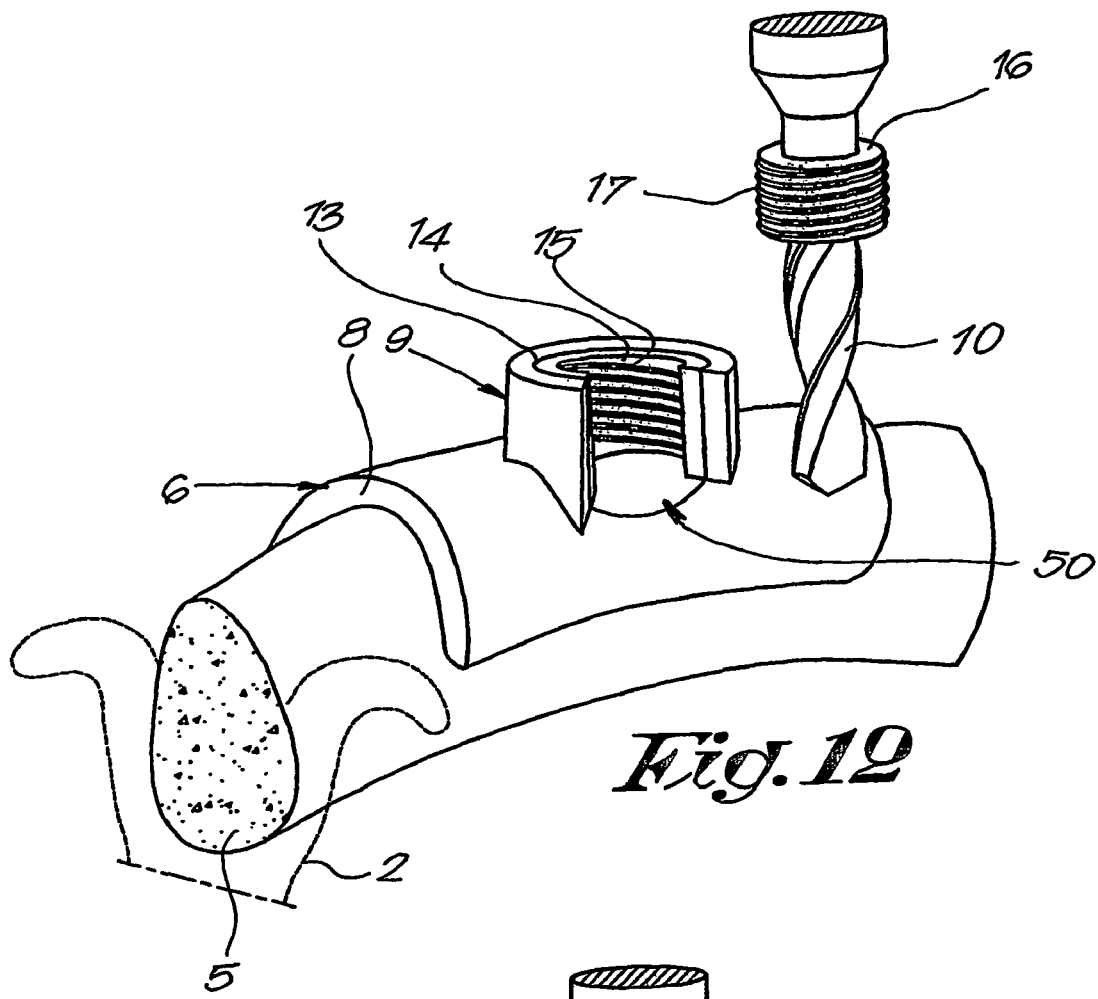
Figure 13:
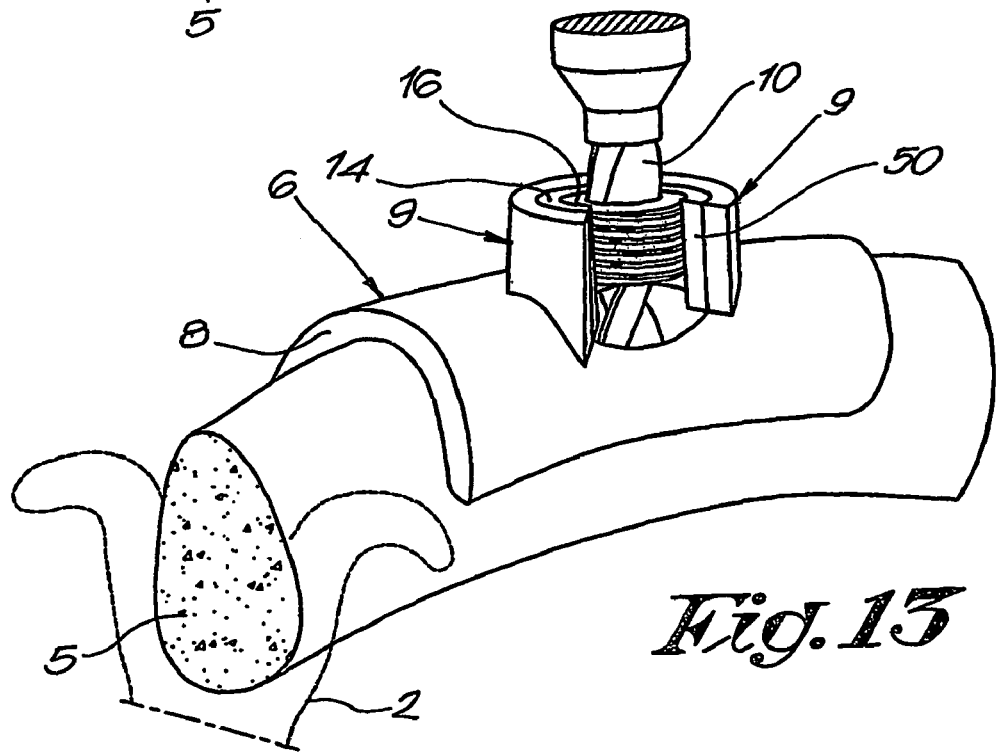

FIGS. 9 to 11 further illustrate a technique which can be applied according to the invention;

FIGS. 12 and 13 show a special embodiment of a drill jig according to the invention, in combination with a drill, for two different positions of the drill.

With the intention of realizing a superstructure, a diagnostic setup of the future teeth will first be made. This is normally done in an articulator, i.e. an appliance in which two teeth molds or plaster models/casts can be positioned in correct relation to one another enabling the simulation of realistic jaw movement. The diagnostic setup is made on the plaster models of the remaining teeth or gums that indicates the future positions of the teeth.

Figure 1:
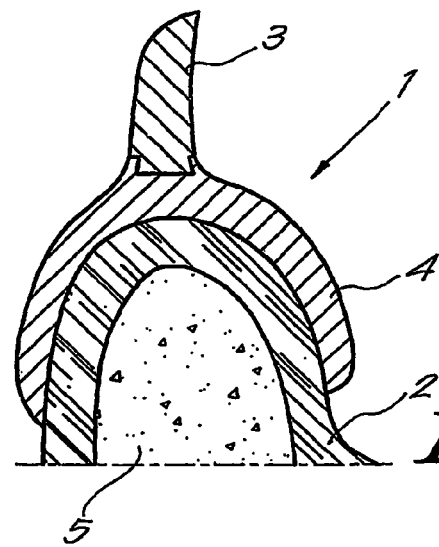
FIG. 1 represents a cross-section of a scan prosthesis.

The same test arrangement is also copied in a radio-opaque material in order to make a scan prosthesis 1, as represented in FIG. 1, the purpose of which will become clear from the further description.

According to a variant of the method, instead of realizing this diagnostic setup in a mechanical articulator, the test arrangement can also be made virtually, with a computer, by means of what is called a 'virtual articulator' which can simulate the movements of the upper jaw in relation to the lower jaw.

In this case, the jaws of the patient or a cast thereof will be scanned, for example with a laser scanner. The two scanned jaws are positioned in relation to one another by registering the respective teeth surfaces on each other, or by scanning one of the jaws with a moldable paste on top of it, such that the surface of one jaw corresponds exactly to the other jaw.

Next, teeth can be chosen from a digital library and positioned in those places where teeth are missing.

After this preliminary stage, preferably as a first step of the actual method, a computer planning is made in view of the placement of the implants.

This can be done for example by first scanning the patient with a computed tomography scanner, CT-scanner in short, and by simulating the implants on the CT-scans, as described in the Belgian patent No. 1.011.205.

It is useful that the patient is scanned with what is called a scan prosthesis 1 as represented in FIG. 1. This is a copy of the loose prosthesis of the patient or of the diagnostic setup made by means of an articulator. This scan prosthesis 1, which is placed on the gums or mucosa 2 during the scanning, is made of a radio-opaque material which is thus visible in the CT-images, whereby the teeth 3 of this scan prosthesis 1 have another degree of opacity than the base part 4 supported on the gums or the mucosa 2, which covers the bone of the patient.

A typical embodiment is one in which the teeth 3 are made of acrylic resin mixed with 30% of barium sulfate, while the rest of the prosthesis 1 is made of a mixture of acrylic resin and 10% of barium sulfate. This offers the advantage that the teeth 3 are nicely visible in the CT-scan images and can thus be segmented separately in a simple manner. In addition the shape of the gums 2 will also be visible, as the base part 4 of the scan prosthesis 1 can be identified and delineates the gums and its lower side represents the shape of the gums. Furthermore, the shape of the surface of the bone 5 is perfectly visible by means of the CT-scan.

Next, a drill jig 6 is made in function of the aforesaid planning. This drill jig can possibly also serve as a fitting jig, since the implants 7 can be placed by means of it. Implant placement can possibly also be done with a separate fitting jig.

The drill jig 6, and possibly the fitting jig, can for example be made by means of Rapid Prototyping techniques, as described in the Belgian patent No. 1.011.205.

Figure 2:
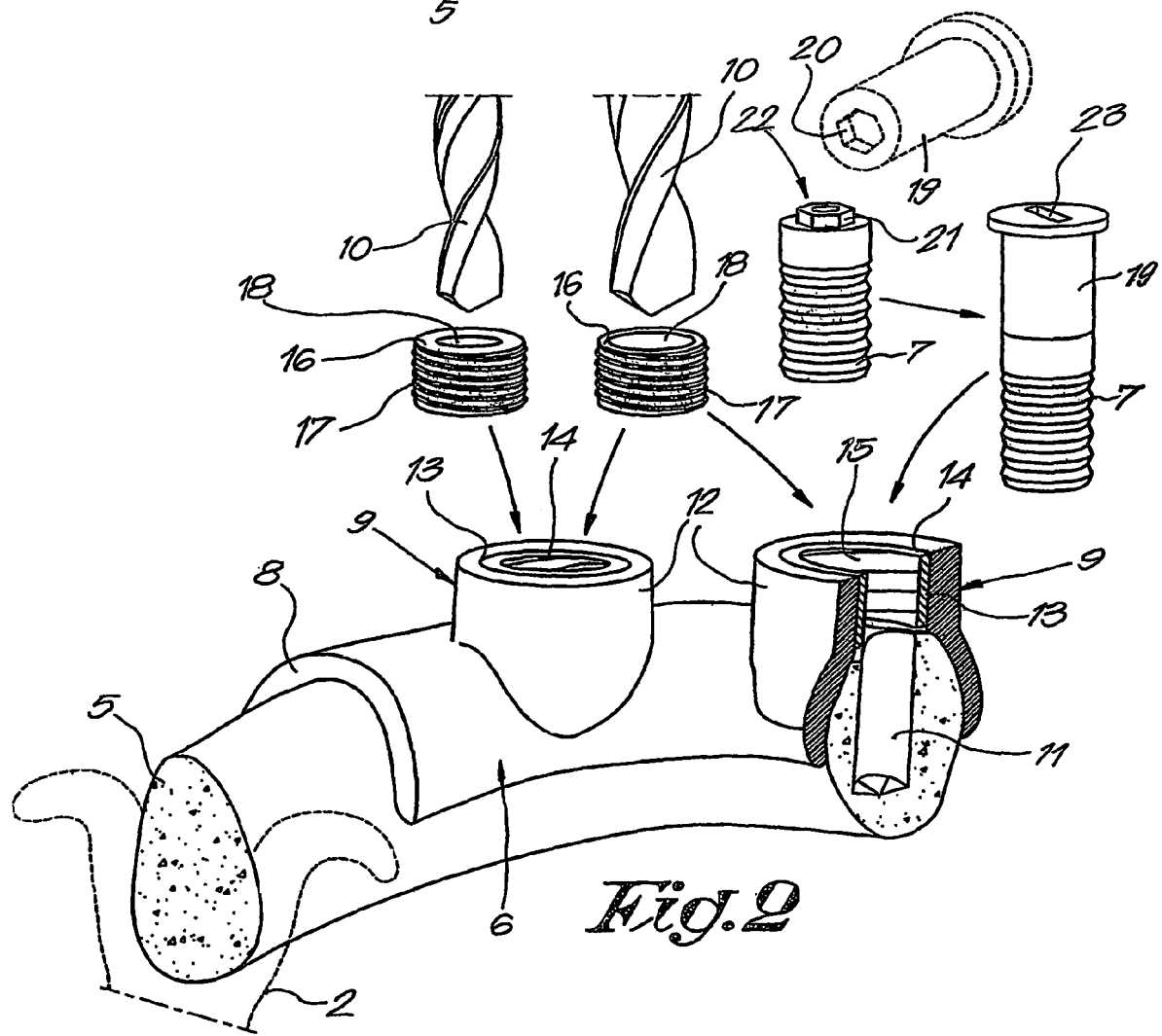
FIG. 2 represents the use of a drill jig as a fitting jig while the method according to the invention is being applied.

According to FIG. 2, the drill jig 6 fits on part 8 of the bone 5 of the patient (after the gums 2 have been opened) and enables pre-operative transferral of the drill directions in conformity with the planning of the surgeon. To this end, the drill jig 6 has ducts 9 for one or several drills 10.

It should be noted that the bone 5 may have a very irregular surface. As the drill jig 6 is designed based on data coming from the CT-scan, the part of the jig in contact with the bone will have an inner surface 8 which always follows the shape of the irregular surface very precisely. The result is that there will always be an accurate positioning.

It should also be noted that, according to a variant, said drill jig, fitting jig and possibly even said positioning jig, can be provided with a contact part which is not or not solely designed to be supported on the bone 5, but (also) cooperates with parts of the gums 2 and/or remaining teeth of the patient The drill jig 6 is used when drilling holes 11 for implants 7.

The drill jig 6 has been designed such that it can be used for all implants 7. This drill jig 6 is put only once on the patient and is possibly screwed down temporarily.

The ducts 9 are, as shown, preferably composed of several parts. First, there are a number of guiding tubes 12, preferably in the form of collars, which make up one piece, together with the contact part of the drill jig 8. These tubes or collars 12 provide openings or passages 13 in which a bush 14 is fixed, made, for example, of metal. The bush 14 is screwed or glued in the opening 13 and provided with screw thread 15 on the inside which makes it possible for interchangeable bushes 16 with external thread 17 to be screwed in.

By using bushes 16 having the same outer diameter but with different internal diameters 18, it becomes possible to guide drills 10 having different diameters. FIG. 2 represents two drills 10 having different diameters and two corresponding bushes 16.

If, as represented, the drill jig 6 is also used as a fitting jig, all the bushes 16 are unscrewed from the drill jig 6 before the implants 7 are placed, and implant holders 19—whose outer diameter corresponds to the inner diameter of the bushes 14—are put on the implants 7. When an implant 7 is placed through the opening 13, the duct guides the implant 7.

Such an implant holder 17 can be realized in different ways. As shown in FIG. 2, it may simply consist of a cylindrical body that at its lower end, for example by means of a recess 20, connects, for example, to the hexagon shaped screw 22 of the implant 7 on fixture level 21, and has a groove 23 on its top side for placing a screwdriver.

It is also possible to manufacture different drill jigs or fitting jigs corresponding to a drilling sequence, whereby every jig is used for guiding a single drill. According to this last method, a different jig with the appropriate diameters for each of the drills 10 or for each type of implant 7 is placed on the patient one after the other.

Drilling of the holes 11 and placing of the implants 7 "as such" can never be performed with the required precision to allow immediate placement of a premanufactured superstructure: the implants 7 will be positioned accurately within a couple of tenths of a millimeter at the most in relation with regards to the planning.

In order to solve this problem, one can use intermediate discs or glue/cement the superstructure on the implants 7 or abutments.

Figure 3:
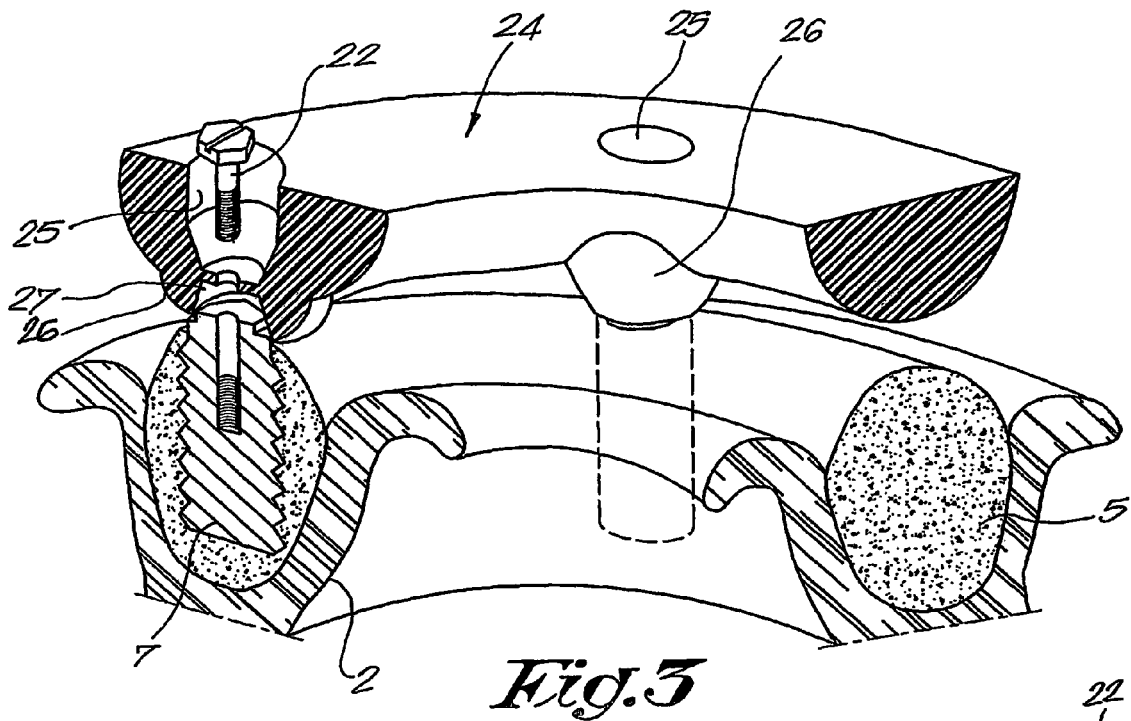
FIG. 3 represents the use of a positioning jig which can be applied according to a possibility of the invention.

The problem is preferably solved according to the present invention by means of positioning a jig 24 that draws the implants 7 nearer and nearer to the correct place, as will be further explained hereafter by means of FIG. 3. A combination of the preceding manners is also possible.

The positioning jig 24 is manufactured in function of the computer planning of the implants 7, with technologies that offer the same precision or possibly are identical to the ones used for manufacturing the superstructure. It preferably consists, as shown in FIG. 3, a body with apertures or passages 25 intended for screws 22 that can be screwed into the implants 7. These apertures 25 and the accompanying screws 22, which needn't necessarily be the same as in FIG. 2, have such a shape that, when the screws 22 are tightened, they are forced into a specific position, such that the implants 7 are aligned in relation to the positioning jig 24. To this end funnel-shaped apertures 25 can be applied.

The positioning jig 24 is screwed onto the implants 7 in a sequential manner. Because of the conical shape of the apertures 25 the implants 7 are forced into the desired position for fitting the superstructure when the screws 22 are successively tightened.

The lower side of the positioning jig 24 must not necessarily be adjusted to the shape of the bone 5 or possibly the gums 2 of the patient. As the drilling and the implant placement have been done in function of the patient, the positioning jig 24 is only necessary for fine-tuning the positions. The small adjustments will assure a perfect correspondence between the implants 7 and the superstructure at fixture level or alternatively—if abutments are used—at abutment level.

As shown, local supporting parts 26 may be provided on the lower side of the positioning jig 24.

In principle, the positioning jig 24 may have the same overall shape as the superstructure. It does not have teeth however. Moreover, the positioning jig 24 may have guiding parts 27 where it connects to the implants 7. These parts guide the implant fixtures 21 or the abutments placed upon them when the implants are drawn into place.

In addition special abutments, can be placed on the implants 7. Such abutments may have a ball joint on top of which a small with internal threading (or similar) allows connection to other structures to be made. This way, large angular deviations as well as larger positioning errors can be rectified.

The function of the positioning jig 24 can also be assumed by the superstructure itself. In this case, the superstructure will draw the implants 7 into the required position. If the bone 5 is rather soft, this will be done while the superstructure is being anchored to the implants.

If the bone 5 is rather hard, for example in the lower jaw, the implants 7 will not shift immediately. This will cause stresses in the superstructure. However, these stresses will gradually disappear, as the superstructure slowly makes the implants 7 shift. Indeed the bone 5 will react to the strains caused by the implant shift and will be slightly remodeled.

The positioning jig 24 can be manufactured by a number of techniques, for example, computer-controlled CNC milling in metal (CoCr, Ti, etc.), molding techniques based of on a master mold made of wax, or CAD/CAM techniques.

Provided some minor adjustments are made, the positioning jig can also be used as an intermediate fitting jig. This intermediate jig can be used for all the implants 7, with the exception of those that were placed first. Such an intermediate fitting jig 28 is represented in FIG. 4.

When one, two or at the most three implants 7 have been placed with the ordinary fitting jig, for example the combined drill jig/fitting jig 6, the intermediate fitting jig 28 can be anchored to those implants. The intermediate fitting jig 28 has features 29, on the one hand, enabling a connection with implants 7 that have already been placed, and features 30, on the other hand, which make it possible to form a duct for one or several drills 10 and/or one or several implant holders 19.

In the given example, the features 29 consist of openings or passages 31 which can be made in a similar manner as the openings 25 and which make it possible for the fitting jig 28 to be fixed on the implants 7 that have already been placed, by means of screws 22 or in any other way.

Figure 4:
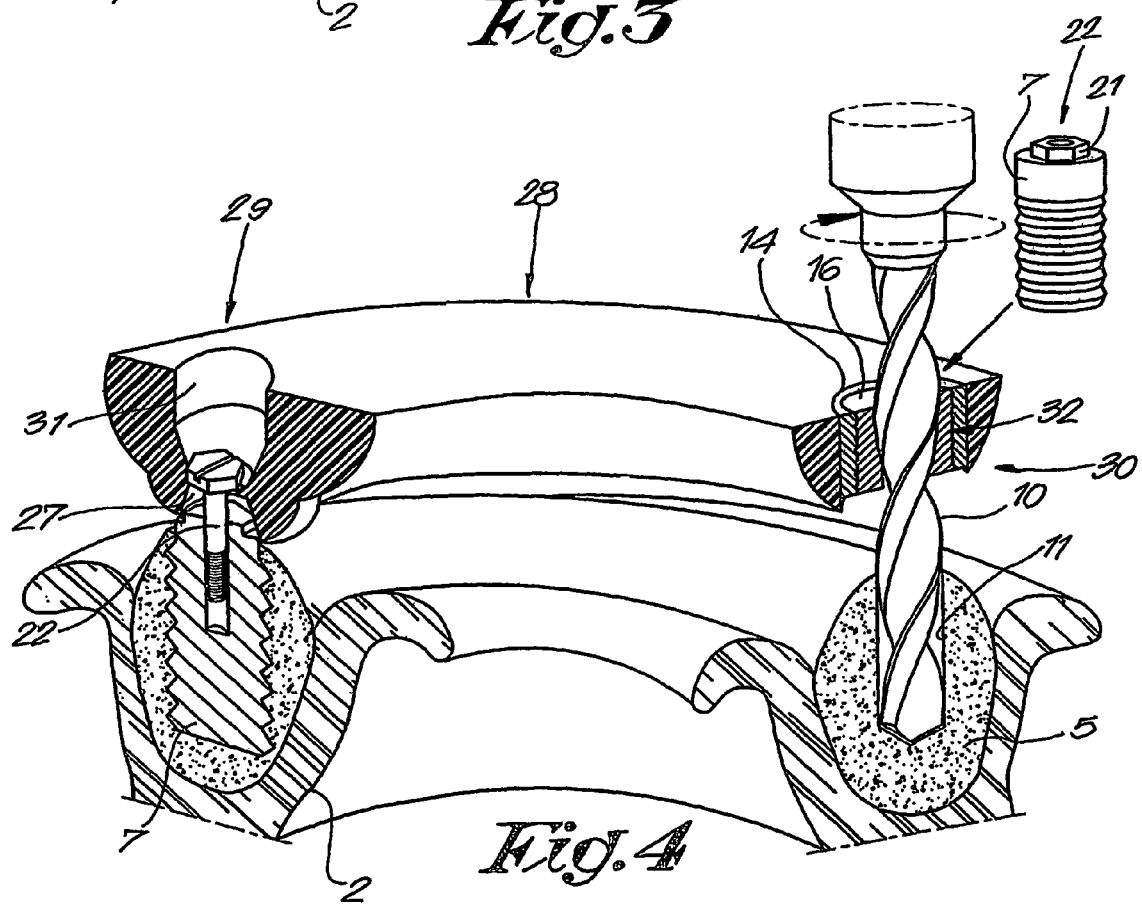
FIG. 4 represents the use of an intermediate fitting jig which can be applied according to a possibility of the invention.

The features 30 include ducts 32 which are comparable to the ducts 9, in which a bush 14 can be provided that fit interchangeable bushes 16, such that the ducts 32 can be used in an analogous manner as the drill jig 6 from FIG. 4, both to guide drills for making additional holes 11 and to guide the implants 7 during their placement.

It is clear that in FIG. 4, only a part of the fitting jig 28 is represented, and that, in reality, it will be fixed on at least two implants 7 that have already been placed. As there is only a limited number of implants 7, it is not difficult to fix the intermediate fitting jig 28 upon them.

As a final step, the superstructure itself is manufactured in function of the planning.

As the exact coordinates and directions of the implants are known, the superstructure can be made with great accuracy. This may be done for example by means of CNC processing or by means of CNC in combination with traditional molding methods. An example of the manufacture of such a superstructure 33 will be described hereafter with reference to FIGS. 5 to 9.

A fixed superstructure 33 consists of two parts. A first part 34 fits on the implants 7 and is preferably designed and manufactured by means of a digital mold cast 35, as will be further described in detail. The second part 36, upon which the teeth 37 are modeled, is produced by means of for example the digital articulator or a scan prosthesis 1.

Figure 5:
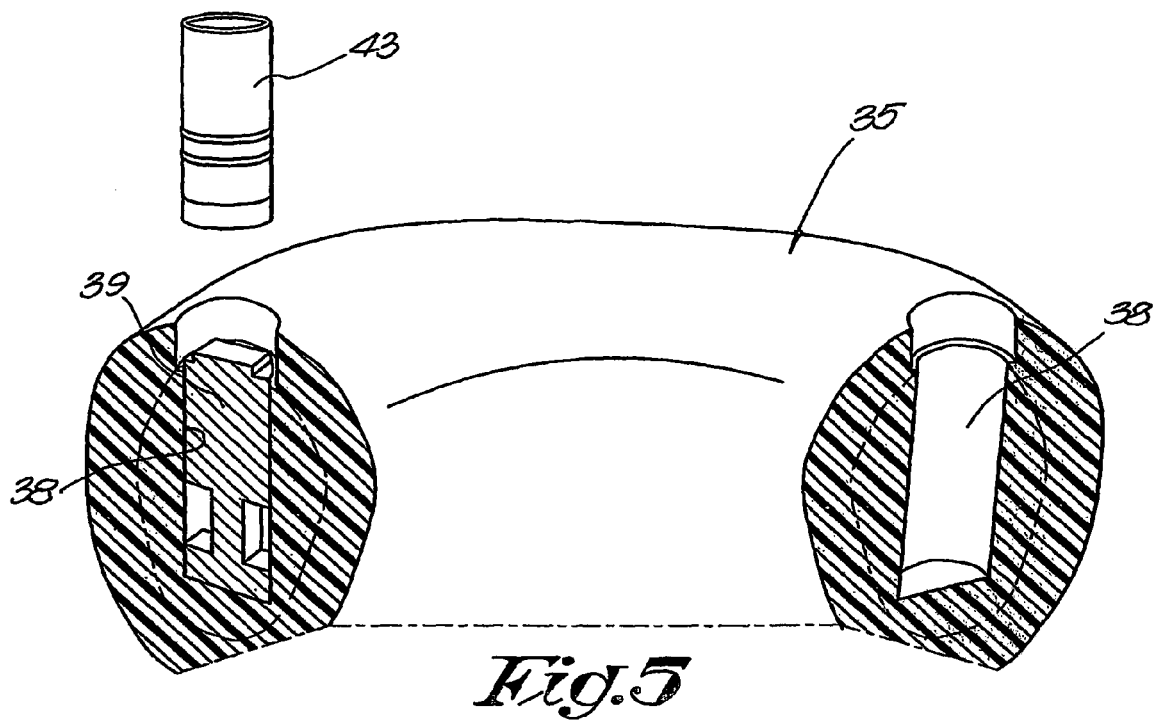
FIG. 5 represents a part of a digital cast which may be used according to the invention.
Figure 7:
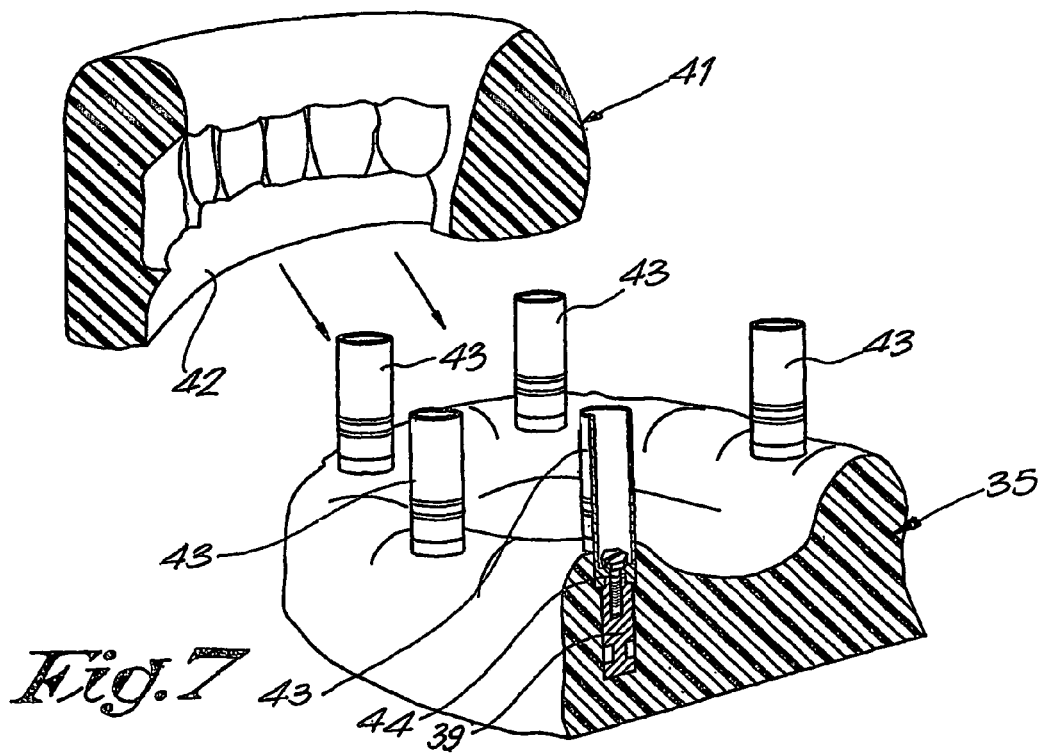
FIG. 7 shows how the key from FIG. 6 and the digital cast from FIG. 5 can be combined.

The digital cast 35, a part of which is represented in FIG. 5, as well as a larger part in FIG. 7, can for example be made by means of rapid prototyping on the basis of the digital data of the aforesaid CT-scan and the computer planning. The scan prosthesis 1 hereby provides information about the gums 2, and the computer planning provides information regarding the positioning of the implants or any abutments fixed upon the latter. Thus, it is possible to build such a digital cast 35, which is in fact a one-piece model representing both the gums 2 and the bone 5 of the patient.

Also, holes 38 are left in the digital cast 35—based on the computer planning—in which implant replicas 39 can be fixed.

Figure 6:
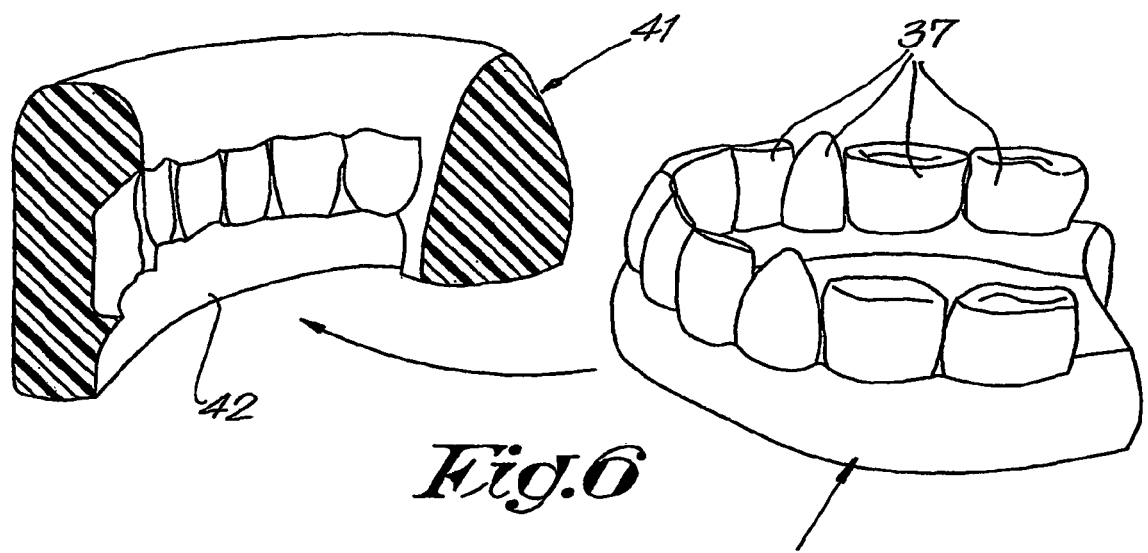
FIG. 6 represents the production and use of a digital key.

Thus, a model is obtained, having the shape of the gums 2, and in which implant replicas 39 are found. This is exactly the same as a traditional, manually made cast which is normally used in the laboratory to produce a superstructure. The laboratory can thus, continue working the way it is used to. It is for example, possible to screw gold cylinders onto the replicas, cast a frame (for example, a golden one), thus forming the above-mentioned part 34. Other CAD/CAM techniques can be used by measuring the model again. In order to obtain the desired shape of the teeth 37 in the superstructure 33, a diagnostic setup 40 of the teeth 37 is made in an articulator (FIG. 6). The teeth 37 are hereby placed in an aesthetic manner in functional relation to both the antagonists and the existing teeth in the same jaw half.

A mold of the teeth 37 in the setup 40 is made which will further be referred to as 'key' 41. This key 41 has a part 42 which precisely delineates the gums 2.

By means of this key 41, the shape of the teeth 37 is transferred to the digital cast 35, or possibly to a similar cast made in another manner, by positioning said is key 41, as represented in FIG. 7, on said cast. The key 41 fits on the digital cast 35, since an identical shape of the gums 2 is used as the basis.

By positioning the mold, in particular, positioning the digital cast 35 and the key 41 against one another and possibly by fixing them against one another, an entire model is obtained which mimics the surface of the gums 2 on the one hand, and which represents a negative of at least the front side of the teeth 37 on the other hand by means of the key 41. Based on this model, a dental technician will be able to build the superstructure 33.

According to an important variant, the key 41 can also be built in a digital manner on the basis of the computer planning. As the shape of the teeth 37 and the shape of the gums 2 are known in the digital model which has been made beforehand with the computer, it is possible to realize a digital key, preferably by means of rapid prototyping, analogous to the above-mentioned key 41, which thus also fits on the digital cast 35, on the basis of said digital model.

By taking an offset of the shape of the teeth 37, it is possible to immediately realize the shape of the metal frame, or of the part 34. Taking an offset means that a key is realized in which the surface corresponding to the outer shape of the teeth 37 is shifted somewhat inwardly. Thus, it is possible to realize a metal shape following the contour of the teeth 37 but situated somewhat more inwardly. By then providing teeth plates upon it and/or by providing a texture over it and/or a porcelain coating, it is possible to provide teeth on the superstructure 33. This is also indicated with reference 37, whose outer side corresponds to the aimed shape.

Such an offset operation thus implies a design compensation to allow an outer layer to be applied, for example made of porcelain, on the metal part of the superstructure 33.

Possibly two digital keys could be manufactured, one corresponding to the shape of the teeth and the other to the shape of the frame to be realized.

Figure 8:
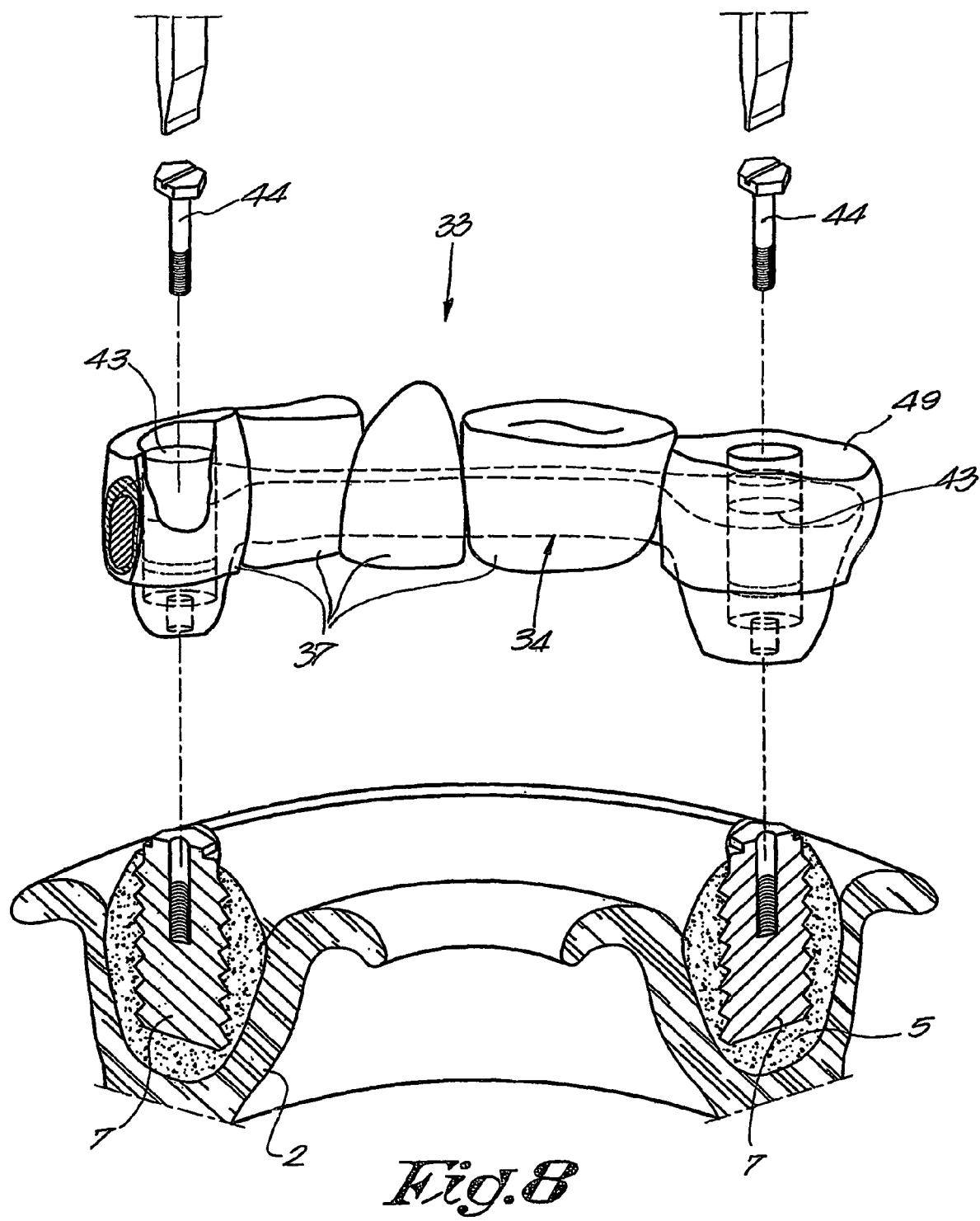
FIG. 8 shows the actual superstructure being fit.

Naturally, when manufacturing the superstructure 33 or a model thereof which can subsequently be cast in metal, anchorage points should be provided in the right places on the superstructure 33 to allow the superstructure to be fixed onto the implants 7. As shown in FIG. 7, little golden cylinders 43 may be placed on the replicas 39 to this end, around which the metal frame of the superstructure 33 is built. These cylinders 43 form openings which make it possible to screw the thus manufactured superstructure 33 on the implants 7 or to fix it upon them in another manner, as represented in FIG. 8. The holes above the screws 44 are sealed with a filler after fixation.

In fact, all sorts of molds and negatives of molds serving as an accessory can be realized by means of computer planning according to the invention, and it is not limited to the above-described digital cast and digital key.

FIG. 9, for example, shows another variant of a mold piece 45 made in an entirely digital manner by means of computer planning. The contour of the part A-B-C represents the shape of a tooth, which is known from the scan data obtained by scanning the scan prosthesis 1. On the basis thereof a contour D-E can be determined which has been shifted slightly (e.g. which is offset in relation to the contour B-C). Also the contour F of the bone 5 is known from the scan data, while the contour G of the holes 11 is known from the computer planning. Based on this information a mold piece 45 can thus be built whose contour part A-D-C and the contours G and F can be realized with great accuracy. The intermediate contour E-H can be formed by filling the space 46, for example via thermojet.

On the basis of the then obtained mold piece 45 a piece 47, with a section as given in FIG. 10, can be made in wax or another modeling material. This piece 47 can then be cast in metal, so that a piece 48 as in FIG. 11 is obtained, upon which teeth plates or a porcelain layer 49 can be provided in order to form the outer side of the teeth of the superstructure 33.

According to yet another variant, the shape of the superstructure itself or of a part thereof can be directly digitally converted to a model, for example by realizing the piece 47 by means of direct prototyping.

According to yet another possibility, the actual superstructure 33, or at least the metal part thereof, is realized immediately by using the digital data available via the scans and computer planning, to for example form the metal frame of the superstructure 33 directly out of metal, for example by means of CAD/CAM techniques. In practice, use can possibly be made to this end of a five-axis milling technique in titanium.

FIGS. 12 and 13 show a special embodiment of a drill jig according to the invention, wherein at least one duct 9 is laterally open, in other words is provided with at least one lateral opening 50, which opening allows the lateral insertion of a drill 10.

In case the duct 9 is provided with a collar 12 and a bush 14, the opening 50 preferably extends through the wall of this collar 12 and bush 14.

Hereby, the above said interchangeable bushes 16 can be placed over the drill 10 prior to insertion and placed in the duct 9 by sliding and turning them over the drill 10 and/or automatically as a result of the drilling action. Hereby the bushes 16 provide a guidance for the drill 10.

The lateral opening 50 allows that the duct 9 is more easily accessible by a drill 10.

It is clear that the drill jig 6 of FIGS. 12-13 can also be used as a fitting and/or positioning jig.

It is also clear that, according to the invention, a drill jig 6 with such a lateral opening 50 can be applied in combination with the above said methods for placing implants, as well as in combination with any other method for placing implants, in which a computer planning may be used or not.

Furthermore, it is clear too that such lateral opening 50 can be used in combination with interchangeable bushes 16 or not. Moreover, such opening 50 can be used in combination with bushes 14 or not, or can be used in combination with any other additional accessories.

The present invention is by no means limited to the above-described embodiments given as an example and represented in the accompanying drawings; on the contrary, such a method for placing and manufacturing a dental superstructure can be made in all sorts of variants while still remaining within the scope of the invention.

The invention claimed is:

1. A method for placing a dental superstructure, said method comprising the steps of:
   placing on the jaw of a patient a drill jig having several ducts with vertical openings for guidance of a drill, wherein the ducts comprise a lateral opening for lateral insertion of the drill and wherein the ducts comprise a thread on the inside;
   laterally inserting the drill into at least one of the ducts by passing a portion of the drill through the lateral opening, wherein one of a series of interchangeable bushes comprising an external thread corresponding to the thread on the inside of the duct and different internal diameters for working with different drill diameters is placed over the drill prior to its insertion into the duct; and
   after the drill has been inserted into the duct, placing the bush in the duct while drilling to provide guidance of the drill.

2. The method according to claim 1, wherein the bushes are unscrewed from the drill jig before implants of the dental superstructure are placed, and implant holders for holding the implants are provided, wherein the outer diameter of the implant holders corresponds to the inner diameter of the bushes for providing guidance of each implant when placed through the vertical opening.

3. The method according to claim 1, wherein the drill jig is also used as a positioning jig for positioning implants in a position for fitting the dental superstructure.

4. The method according to claim 1, wherein use is at least made of a positioning jig for positioning implants in a position for fitting the dental superstructure, wherein the positioning jig is adapted as an accessory to force the implants into a specific position after they have been placed.

5. The method according to claim 4, wherein said positioning jig is provided with at least one aperture for a screw, said aperture adapted to be screwed into the implants, wherein said aperture has such a funnel-like shape that, when the screw is tightened, the accessory is forced into the specific position.

6. The method according to claim 4, wherein computer planning is used to form at least a part of the drill jig and/or at least a part of a molding piece for the drill jig.

7. The method according to claim 1, wherein use is at least made of an intermediate positioning jig as an accessory which at least has features adapted for connection to at least one implant that has already been placed, and features forming a duct for a drill and/or for an implant or features forming an implant placed on an implant holder.

8. The method according to claim 1, wherein said drill jig is formed by means of data obtained by scanning a patient being provided with the dental superstructure and by means of a computer planning using said data.

9. The method according to claim 8, wherein use is at least made of one of the following or a combination of two or more of the following elements:
   an accessory in the shape of a digital cast representing the general shape of a bone and/or of gums, wherein the positions of implants are represented, in particular by means of implant replicas, holes or the like;
   an accessory in the shape of a key with a part representing the shape of teeth and a part which is a negative of at least a part of the shape of the gums;
   an accessory in the shape of a mold piece with contour parts (A-B-C) and possibly a shifted part (D-E) adjusted to the shape of the teeth of the superstructure to be formed, and with contours (G-F) representing the shape of holes for the implants and of the bone respectively;
   an accessory in the shape of a piece made directly out of a modelling material and which has the shape of the superstructure or of a part thereof.

10. The method according to claim 1, wherein use is made of a key representing a mold of teeth, which is obtained by means of a mold on the basis of a diagnostic arrangement of the teeth, and wherein use is made of a digital cast representing the general shape of a bone together with gums, and in which the positions of implants are represented, in particular by means of implant replicas, whereby the key and the digital cast fit against one another.

11. The method according to claim 1, wherein the superstructure, a frame of the superstructure, or a portion of either thereof is built directly on the basis of digital data obtained from a computer planning or from a scan of at least a portion of the patient's teeth or jaw.

12. The method according to claim 11, wherein the superstructure, or at least said part thereof, is realized by means of rapid prototyping techniques.

13. The method according to claim 1, wherein the superstructure is made prior to placement of implants, and wherein the superstructure is fixed on the implants before they have grown in, either immediately after or shortly after the placing of these implants, whereby the superstructure functions as an element for the application of an immediate loading technique.

* * * * *

UNITED STATES PATENT AND TRADEMARK OFFICE
CERTIFICATE OF CORRECTION

PATENT NO. : 8,038,440 B2
APPLICATION NO. : 10/546702
DATED : October 18, 2011
INVENTOR(S) : Swaelens et al.

Page 1 of 1

It is certified that error appears in the above-identified patent and that said Letters Patent is hereby corrected as shown below:

Column 3, Line 30, replace "to force the forcing" with --the forcing--;

Line 33, replace "whereby said the accessory" with --whereby the accessory--.

Column 6, Line 58, replace "based of on a" with --based on a--.

Column 7, Lines 55-56, replace "It is for example," with --It is, for example,--.

Column 9, Line 40, replace "with such a" with --with a--;

Line 41, replace "the above said methods" with --the above methods--.

Signed and Sealed this
Fifth Day of June, 2012

David J. Kappos
*Director of the United States Patent and Trademark Office*